(12) United States Patent
Day et al.

(10) Patent No.: US 7,605,255 B2
(45) Date of Patent: Oct. 20, 2009

(54) NON-ANIMAL BASED LACTOSE

(75) Inventors: Donna Day, Edmonton (CA); Minghui Du, Edmonton (CA); Roberto Mendez, Edmonton (CA); Darol Maunder, Edmonton (CA)

(73) Assignee: Alberta Research Council Inc., Edmonton, Alberta (CA)

( * ) Notice: Subject to any disclaimer, the term of this patent is extended or adjusted under 35 U.S.C. 154(b) by 583 days.

(21) Appl. No.: 11/427,543

(22) Filed: Jun. 29, 2006

(65) Prior Publication Data

US 2008/0004438 A1   Jan. 3, 2008

(51) Int. Cl.
 *C07H 3/04* (2006.01)
(52) U.S. Cl. ............. 536/124; 536/123.13; 127/31
(58) Field of Classification Search ............ 536/123.13, 536/124; 127/31
See application file for complete search history.

(56) References Cited

U.S. PATENT DOCUMENTS

| | | | |
|---|---|---|---|
| 1,954,602 A | 4/1934 | Supplee et al | |
| 1,956,811 A | 5/1934 | Sharp | |
| 2,182,618 A | 12/1939 | Sharp | |
| 2,182,619 A | 12/1939 | Sharp | |
| 3,721,585 A | 3/1973 | Francis et al. | |
| 4,083,733 A | 4/1978 | Asano et al. | |
| 5,162,517 A | 11/1992 | Darsow | |
| 5,180,674 A | 1/1993 | Roth | |
| 5,641,872 A | 6/1997 | Darsow | |
| 5,945,314 A | 8/1999 | Prieto et al. | |
| 6,124,443 A | 9/2000 | Darsow | |
| 6,177,598 B1 * | 1/2001 | Brunner et al. | ............. 568/863 |

OTHER PUBLICATIONS

Oh et al, Conformal Analysis and Molecular Dynamics Simiulation of Lactose, Bull. Korean Chem. Soc., (1995) vol. 16, No. 12, pp. 1153-1162.*

* cited by examiner

*Primary Examiner*—David M Brunsman
(74) *Attorney, Agent, or Firm*—Bennett Jones LLP

(57) ABSTRACT

A synthetic procedure for the preparation of non-animal based lactose from 4'-epimeric analogue of lactose by use of orthogonal protecting groups, formation of a suitable leaving group at the 4'-position, stereochemical inversion by nucleophilic attack and deprotection.

8 Claims, 1 Drawing Sheet

NON-ANIMAL BASED LACTOSE

FIELD OF THE INVENTION

The present invention relates to the synthesis of non-animal based lactose via a 4'-epimeric analog of lactose.

BACKGROUND

Carbohydrates play a central role in various functions within living organisms, such as, in metabolism, as an energy source, as biological markers, for protection against the environment, as receptor substances and as antigenic determinants (for example blood group antigens). Carbohydrate structures are also important for the stability, activity, localization, immunogenicity, and degradation of glycoproteins; as receptors when bound to cell surfaces for pathogens, proteins, hormones, toxins and during cell-cell interactions; and oncogenesis.

Oligosaccharide derivatives, such as, deoxy-, phosphor sulphate-, derivatized amino or thio groups, are of high interest for pharmaceutical or diagnostic application of carbohydrates, to modify the metabolism of the substances and/or to increase the biological effect of the natural substance.

Lactose is a disaccharide found in the milk of animals and was initially known as milk sugar as it makes up about 2-8% of the solids in milk. It consists of a galactose subunit and a glucose subunit bonded through a β1-4 glycosidic linkage. Both sugar subunits are present in the pyranose form in lactose.

The present invention relates to a novel production process for non-animal based lactose by pure chemical synthesis. At present, there is no known source for animal free lactose product.

SUMMARY OF THE INVENTION

In one aspect, the invention comprises a novel synthetic procedure for the preparation of non-animal based lactose via cellobiose intermediates. The procedure comprises a method for the synthesis of lactose from a 4'-epimeric analog of lactose by use of orthogonal protecting groups, formation of a suitable leaving group at the 4'-position, stereochemical inversion by nucleophilic attack and deprotection.

BRIEF DESCRIPTION OF THE DRAWINGS

Embodiments of the invention may now be described with reference to the following drawing.

DETAILED DESCRIPTION OF PREFERRED EMBODIMENTS

Figure 1:
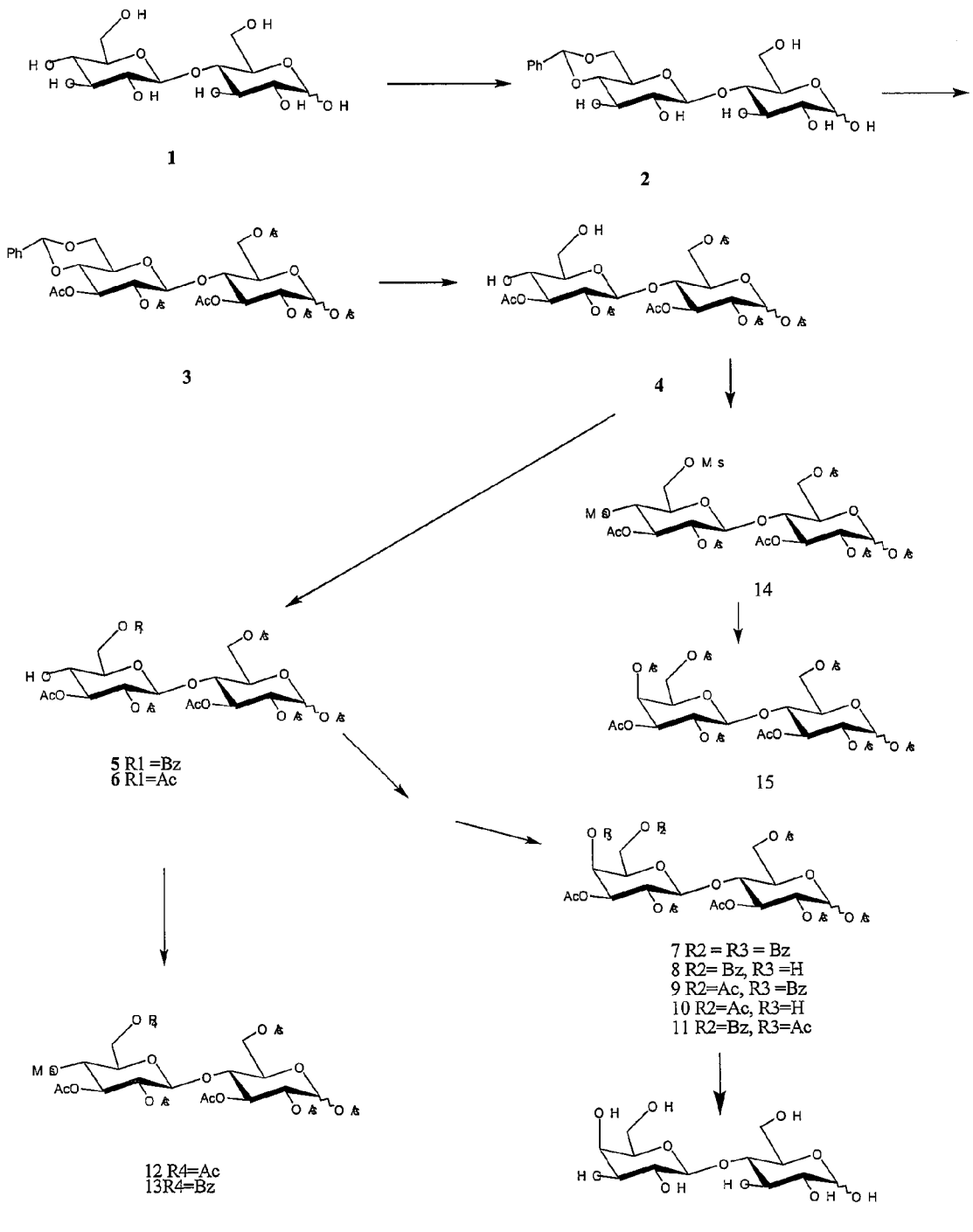
FIG. 1 shows one embodiment of a synthetic route for the preparation of lactose, starting with cellobiose.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

As used herein, "epimers" means molecules that differ from each other at one stereocenter, thus, diastereomers that differ from each other in stereochemistry at only one of many stereocenters are called epimers. As used herein, a "stereocenter" means a carbon atom that has four different types of atoms or groups of atoms attached to it. As used herein, a "nucleophile" means a reagent that donates a pair of electrons. As used herein, "stereoisomers" means molecules that have the same atomic connectivity but different atomic arrangement in space. As used herein, a "protecting group" means a chemical group that is inert to the conditions of a reaction (or reactions) that is to be carried out as part of a synthetic pathway. As used herein, a "leaving group" means a stable species that can be detached from a molecule with its bonding electrons during a displacement reaction. As used herein, "orthogonal protecting groups" means protecting groups that are complementary to each other, such that, each protecting group is independently removable. As used herein, "lactose" means a disaccharide that consists of the pyranose sugars β-D-galactose and β-D-glucose, bonded through a β1-4 glycosidic linkage and may include lactose analogs.

In one embodiment, the synthetic strategy involves use of a 4'-epimeric analog of lactose, where the functional group at C4' can undergo inversion of stereochemistry by chemical manipulation, as the starting material, followed by use of orthogonal protecting groups that would allow isolation and inversion of stereochemistry at the C4', and deprotection to obtain lactose. This strategy allows for an efficient synthetic route, while also resulting in a novel and a purely chemical synthetic route to lactose.

A preferred embodiment of the inventive method disclosed herein starts with cellobiose, which consists of two subunits of glucopyranose linked in a β-configuration. Cellobiose is a 4'-epimer of lactose. As shown in FIG. 1, in one embodiment, the 4',6'-hydroxyl protection of cellobiose with benzaldehyde in the presence of p-toluenesulfonic acid in DMSO, leads to an acetal 2, which can be later removed to allow manipulation of the 4'-hydroxyl. Acetylation of the other hydroxyl groups using acetic anhydride in pyridine leads to 3. Removal of the acetal leads to a per-acetylated moiety 4, with free 4' and 6' hydroxyls. The primary hydroxyl group at the C6'-position cannot undergo stereochemical inversion, but can assist in the inversion of stereochemistry at the C4'-position. Multiple routes for inversion of stereochemistry are possible at this point. A few examples are depicted in FIG. 1.

One route involves the selective 6'-hydroxyl protection by acetyl 6 or benzoyl 5 protecting groups. The subsequent conversion of the 4'-hydroxyl group into a suitable leaving group followed by nucleophilic attack leading to inversion can be performed in a single step as shown in FIG. 1. For example, the benzoyl-protected 5 can be converted to a triflate in situ, followed by reaction with sodium benzoate to form 7 or sodium nitrite to form 8. Alternatively, the 6'-acetyl protected cellobiose 6 can be reacted analogously to form 9 or 10. Also possible is reaction of the in situ formed triflate of 5 with tetracetylammonium acetate in acetonitrile to form 11.

Another route involves the isolation of the mesylate 12, 13 or 14 from 6, 5 or 4, respectively; followed by inversion of stereochemistry.

The esters 7, 8, 9, 10, 11 or 15 can be hydrolyzed using an aqueous basic medium, such as sodium methoxide, followed by neutralization and isolation to obtain lactose 16.

Embodiments of the present invention are described in the following Examples, which are set forth to aid in the understanding of the invention, and should not be construed to limit in any way the scope of the invention as defined in the claims which follow thereafter.

EXAMPLES

Example 1

4'6'-O-BENZYLIDENE-CELLOBIOSE 2

To a mixture of cellobiose (350 g) in DMSO (1049 mL) was added benzaldehyde dimethylacetal (245 mL) followed by p-toluenesulfonic acid (16 g). This mixture was heated at 40° C. for 24 h and evaporated, co-evaporated with toluene. The residue was washed with dichloromethane and the crude product 2 was used in Example 2.

Example 2

1,2,3,6,2',3'-HEXA-O-ACETYL-4'6'-O-BENZYLIDENE-CELLOBIOSE 3

The above crude product 2 was acetylated in pyridine (1200 mL) and acetic anhydride (600 mL) for 16 h. After evaporation, the remaining residue was dissolved in dichloromethane and washed with water. The solvent was removed by evaporation to give crude product 3 (683 g), which was used directly in Example 3.

Example 3

1,2,3,6,2',3'-HEXA-O-ACETYL-CELLOBIOS 4

A solution of the above product 3 (321 g) in dichloromethane (643 mL) was cooled at −20° C. Trifluoroacetic acid (90%, 257 mL) was added. Stirring was continued for 1 h at −20° C. The solution was then washed with ice-water and aqueous sodium bicarbonate, dried over sodium sulphate and evaporated. The product was purified though a silica gel column using hexane-acetone 1:1 as eluent to give 4 (150 g) as a foam.

Example 4

1,2,3,6,2',3'-HEXA-O-ACETYL-6'-O-BENZOYL-CELLOBIOSE 5

A solution of 1,2,3,6,2'3'-hexa-O-acetyl-cellobiose 4 (209 g) in dichloromethane (5 L) and pyridine (836 mL) was cooled at −40° C. and benzoyl chloride (45 mL) was added dropwise. Stirring was continued for 1 h at −40° C. to −20° C. and methanol (20 mL) was added. The solution was then washed with water and evaporated. The crude product was dissolved in methyl tert-butyl ether (1200 mL) at 70° C. The solution was then cooled to 4° C. and hexane (1500 mL) was added. The solid product 5 (190 g) was collected by filtration.

Example 5

1,2,3,6,2',3',6'-HEPTA-O-ACETYL-CELLOBIOSE 6

A solution of 1,2,3,6,2'3'-hexa-O-acetyl-cellobiose 4 (1.93 g) in dichloromethane (60 mL) and pyridine (4 mL) was cooled at −30° C. and acetyl chloride (4.87 mL) in dichloromethane (5 mL) was added dropwise. Stirring was continued for 1 h at −30° C. to −20° C. and methanol (1 mL) was added. The solution was then washed with water and evaporated. The crude product was precipitated in ethyl acetate to give 6 (1.3 g).

Example 6

1,2,3,6,2',3'-HEXA-O-ACETYL-4'6'-DI-O-BENZOYL-LACTOSE

A solution of 1,2,3,6,2',3'-Hexa-O-acetyl-6'-O-benzoyl-cellobiose 5 (183 g) in dichloromethane (2280 mL) and pyridine (380 mL) was cooled at −10° C. and trifluoromethanesulfonic anhydride (57 mL) in dichloromethane (915) mL was added dropwise. The reaction mixture was then stirred at room temperature for 1 h and washed with cold water, 2% hydrochloric acid and sat. sodium bicarbonate, dried over sodium sulphate and evaporated. The yellowish foam (220 g) and sodium benzoate (63 g) in DMF (1252 mL) were stirred at room temperature overnight. The mixture was diluted with dichloromethane and filtered. The filtrate was evaporated and the residue was purified by chromatography on silica gel column using hexane-ethyl acetate 1:1 as eluent to give product 7 (78 g).

Example 7

1,2,3,6,2',3'-HEXA-O-ACETYL-6'-O-BENZOYL-LACTOSE 8

A solution of 1,2,3,6,2',3'-Hexa-O-acetyl-6'-O-benzoyl-cellobiose 5 (880 mg) in dichloromethane (17 mL) and pyridine (2.7 mL) was cooled −10° C. and trifluoromethanesulfonic anhydride (0.31 mL) in dichloromethane (3 mL) was added dropwise. The reaction mixture was then stirred at room temperature for 1 h and washed with cold water, 2% hydrochloric acid and sat. sodium bicarbonate dried over sodium sulphate and evaporated. The yellowish foam (1 g) and sodium nitrite (174 mg) in DMF (10 mL) were stirred at room temperature overnight. The mixture was diluted with dichloromethane and filtered. The filtrated was evaporated and the residue was purified by chromatography on silica gel column using hexane-ethyl acetate 1:1 as eluent to give product 8 (320 mg).

Example 8

1,2,3,6,2'3',6'-HEPTA-O-ACETYL-4'-O-BENZOYL-LACTOSE 9

A solution of 1,2,3,6,2'3',6'-Hepta-O-acetyl-cellobiose 6 (30 mg) in dichloromethane (2 mL) and pyridine (0.17 mL) was cooled at −10° C. and trifluoromethanesulfonic anhydride (17 μL) in dichloromethane (0.5 mL) was added dropwise. The reaction mixture was then stirred at room temperature for 1 h and washed with cold water, 2% hydrochloric acid and sat. sodium bicarbonate dried over sodium sulphate and evaporated. The yellowish foam (35 mg) and sodium benzoate (40 mg) in DMF (0.8 mL) were stirred at 50° C. for 3 h. The mixture was evaporated and the residue was dissolved in dichloromethane and washed with water. Evaporation then left product 9 (34 mg).

Example 9

1,2,3,6,2'3',6'-HEPTA-O-ACETYL-LACTOSE 10

A solution of 1,2,3,6,2'3',6'-Hepta-O-acetyl-cellobiose 6 (42 mg) in dichloromethane (3 mL) and pyridine (0.19 mL) was cooled at −10° C. and trifluoromethanesulfonic anhydride (22 mL) in dichloromethane (0.7 mL) was added dropwise. The reaction mixture was then stirred at room temperature for 1 h and washed with cold water, 2% hydrochloric acid and sat. sodium bicarbonate dried over sodium sulphate and evaporated. The yellowish foam (50 mg) and sodium nitrite (60 mg) in DMF (1 mL) were stirred at room temperature overnight. The mixture was evaporated and the residue was dissolved in dichloromethane and washed with water. Evaporation then left product 10 (40 mg).

Example 10

1,2,3,6,2',3',4'-HEPTA-O-ACETYL-6'-O-BENZOYL-LACTOSE 11

A solution of 1,2,3,6,2'3'-Hexa-O-acetyl-6'-O-benzoyl-cellobiose 5 (500 mg) in dichloromethane (10 mL) and pyridine (1.5 mL) was cooled at −10° C. and trifluoromethanesulfonic anhydride (0.4 mL) in dichloromethane (2 mL) was added dropwise. The reaction mixture was then stirred at room temperature for 1 h and washed with cold water, 2% hydrochloric acid and sat. sodium bicarbonate dried over sodium sulphate and evaporated. The yellowish foam (600 mg) and tetraacetylammonium acetate hydrate (230 mg) in acetonitrile (5 mL) were stirred at room temperature overnight. The mixture was evaporated and the residue was purified by chromatography on silica gel column using hexane-ethyl acetate 1:1 as eluent to give product 11 (350 mg).

Example 11

1,2,3,6,2',3',6'-HEPTA-O-ACETYL-4'-O-METHANESULFONYL-CELLOBIOSE 12

A solution of 1,2,3,6,2'3',6'-hepta-O-acetyl-cellobiose 6 (60 mg) in dichloromethane (2 mL) and pyridine (0.5 mL) was cooled at 0° C. and methanesulfonyl chloride (15 µL) was added. Stirring was continued for 3 h at room temperature and methanol (1 mL) was added. The solution was then evaporated and the crude product was purified by chromatography on silica gel using hexane-ethyl acetate as eluent to give 12 (53 mg).

Example 12

1,2,3,6,2',3'-HEXA-O-ACETYL-6'-O-BENZOYL-4'-O-METHANESULFONYL-CELLOBIOSE 13

A solution of 1,2,3,6,2'3'-hexa-O-acetyl-6'-benzoyl-cellobios 5 (300 mg) in dichloromethane (10 mL) and pyridine (1 mL) was cooled at 0° C. and methanesulfonyl chloride (0.2 mL) was added. Stirring was continued for 3 h at room temperature and methanol (1 mL) was added. The solution was then evaporated and the crude product was purified by chromatography on silica gel using hexane-ethyl acetate as eluent to give 13 (160 mg).

Example 13

1,2,3,6,2',3'-HEXA-O-ACETYL-4'6'-DI-O-METHANESULFONYL-CELLOBIOSE 14

A solution of 1,2,3,6,2',3'-Hexa-O-acetyl-cellobiose 4 (140 mg) in dichloromethane (5 mL) and pyridine (0.8 mL) was cooled at 0° C. and methanesulfonyl chloride (0.16 mL) was added. Stirring was continued for 4 h at room temperature and the solution was diluted with dichloromethane, washed with water, dried over sodium sulphate and evaporated to give product 14 (140 mg).

Example 14

1,2,3,6,2',3',4'6'-OCTA-O-ACETYL-LACTOSE 15

A solution of 1,2,3,6,2'3'-hexa-O-acetyl-4'6'-di-O-methanesulfonyl-cellobiose 14 (100 mg) and tetraethylammonium hydrate (30 mg) in DMF (1 mL) was heated at 100° C. for 4.5 h and evaporated. The residue was dissolved in ethyl acetate and washed with water. Evaporation of the solvent left 15 (15 mg).

Example 15

LACTOSE 16

1,2,3,6,2'3'-Hexa-O-acetyl-4'6'-di-O-benzoyl-lactose 7 (800 mg) was treated with sodium methoxide (25%, 2 mL) in methanol (10 mL) overnight. The solid product was filtered and washed with methanol. The methanol solution was neutralized with Amberlite IR 120 H$^+$, filtered and evaporated. The crude product was stirred in ethanol (2 mL) and filtered. Lactose 16 (260 mg) was obtained.

What is claimed is:

1. A method for the synthesis of lactose from a 4'-epimeric analog of lactose by use of orthogonal protecting groups, formation of a suitable leaving group at the 4'-position, stereochemical inversion by nucleophilic attack and deprotection.

2. A method of synthesizing lactose, comprising the steps of:
    a) protecting at least the 4'-epimeric functional group of a 4'-epimeric analog of lactose with a first protecting group;
    b) protecting all other hydroxyl groups with a second protecting group;
    c) removal of the first protecting group;
    d) conversion of the 4'-epimeric functional group into a suitable leaving group;
    e) nucleophilic attack leading to stereochemical inversion at the 4'-position; and
    f) removal of the protecting groups;
    and wherein the first and second protecting groups are orthogonal.

3. The method of claim 2 wherein, the first protecting group is an acetal or ketal.

4. The method of claim 2 wherein, the second protecting group is an ester.

5. The method of claim 2 wherein, the suitable leaving group is a mesylate or triflate.

6. The method of claim 2 wherein, the nucleophilic attack leads to formation of a stereochemically inverted ester.

7. The method of claim 2 wherein, the protecting groups are removed using a basic medium.

8. The method of claim 7 wherein; the basic medium comprises of sodium methoxide.

* * * * *